US011339281B2

(12) United States Patent
Gigras et al.

(10) Patent No.: US 11,339,281 B2
(45) Date of Patent: May 24, 2022

(54) PHOTO-RESPONSIVE SHAPE CHANGING POLYMER COMPOSITION FOR COLORED OPTICAL LENS

(71) Applicant: NAYAM INNOVATIONS PVT LTD, Pune (IN)

(72) Inventors: Tanuj Gigras, Pune (IN); Surendra Ponrathnam, Pune (IN); Gahininath Bharate, Pune (IN); Julia Ann Kornfield, Pune (IN); Mandar Gadre, Pune (IN); Sunil Kumar Chaubey, Pune (IN)

(73) Assignee: NAYAM INNOVATIONS PVT LTD, Pune (IN)

( * ) Notice: Subject to any disclaimer, the term of this patent is extended or adjusted under 35 U.S.C. 154(b) by 11 days.

(21) Appl. No.: 16/758,264

(22) PCT Filed: Oct. 31, 2018

(86) PCT No.: PCT/IB2018/058538
§ 371 (c)(1),
(2) Date: Apr. 22, 2020

(87) PCT Pub. No.: WO2019/087095
PCT Pub. Date: May 9, 2019

(65) Prior Publication Data
US 2020/0347218 A1 Nov. 5, 2020

(30) Foreign Application Priority Data
Nov. 1, 2017 (IN) .............................. 201721038965

(51) Int. Cl.
| | | |
|---|---|---|
| *C08F 2/46* | (2006.01) | |
| *C08F 2/50* | (2006.01) | |
| *C08G 61/04* | (2006.01) | |
| *C08L 33/06* | (2006.01) | |
| *A61F 2/16* | (2006.01) | |
| *A61L 27/16* | (2006.01) | |
| *G02B 1/04* | (2006.01) | |

(52) U.S. Cl.
CPC .......... *C08L 33/062* (2013.01); *A61F 2/1627* (2013.01); *A61L 27/16* (2013.01); *G02B 1/041* (2013.01); *A61F 2250/0001* (2013.01); *A61F 2250/005* (2013.01); *A61L 2430/16* (2013.01); *C08L 2205/025* (2013.01); *C08L 2312/00* (2013.01)

(58) Field of Classification Search
CPC .... C08L 33/062; C08L 33/08; C08L 2666/70; C08L 2312/00; C08L 2205/025; G03F 7/038; G03F 7/005; G03F 7/033; G03F 7/031; G03F 7/105; A61L 27/16; A61L 2430/16; A61F 2/1627; A61F 2/1635; A61F 2250/005; A61F 2250/0001; G02B 1/041; C08K 5/1545; C08K 5/0025
USPC ................. 522/64, 6, 71, 189, 184, 1; 520/1
See application file for complete search history.

(56) References Cited

U.S. PATENT DOCUMENTS

| | | |
|---|---|---|
| 6,200,646 B1 | 3/2001 | Neckers et al. |
| 2006/0052547 A1 | 3/2006 | Jethmalani et al. |
| 2007/0066705 A1 | 3/2007 | Kawaguchi et al. |
| 2012/0268710 A1 | 10/2012 | McGinniss et al. |
| 2015/0168605 A1* | 6/2015 | Ying ....................... G02B 1/043 252/586 |
| 2016/0331868 A1* | 11/2016 | Grubbs ................. A61L 27/047 |

FOREIGN PATENT DOCUMENTS

WO 2019087095 A2 5/2019

OTHER PUBLICATIONS

International Search Report dated Jun. 21, 2019 in International Patent Application No. PCT/IB2018/058538 (2 pgs.).
Written Opinion of the International Searching Authority dated Jun. 21, 2019 in International Patent Application No. PCT/IB2018/058538 (5 pgs.).

* cited by examiner

*Primary Examiner* — Jessica Whiteley
(74) *Attorney, Agent, or Firm* — Shumaker, Loop & Kendrick, LLP

(57) ABSTRACT

Photo-responsive shape changing polymer compositions including photoinitiators that absorb light in the range about 400 nm to about 700 nm, a cross-linked polymer matrix and a polymerizable composition. Photopolymerization of the polymerizable composition sorbed in the cross-linked polymer matrix results in the shape change which manifests in the change in the refractive properties of the composition. The light dose required to effect the shape change; lock-in dose and the photobleaching dose are determined by the choice of the photoinitiator, electron donor and the hydrogen donor. These compositions are useful in the fabrication of coloured lenses, especially intraocular lenses.

27 Claims, 9 Drawing Sheets

PHOTO-RESPONSIVE SHAPE CHANGING POLYMER COMPOSITION FOR COLORED OPTICAL LENS

CROSS-REFERENCE TO RELATED APPLICATIONS AND PRIORITY

The present application claims priority from Indian Patent Application No. 201721038965 filed on 1 Nov. 2017 and PCT Application no. PCT/IB2018/058538 filed on 31 Oct. 2018.

BACKGROUND OF THE INVENTION

This invention relates generally to photo-responsive shape changing polymer compositions. Particularly, this invention relates to photo-responsive shape changing polymer compositions that can be reshaped by exposing to a dose of visible light. It also relates to colored intraocular lenses made from photo-responsive shape changing polymer compositions that can be photobleached, and their method of use.

Optical lenses are used in a wide variety of applications including lenses for optical instruments such as cameras and telescopes to intraocular lenses (IOLs) for use in the human eye. Most optical lenses are fabricated for pre-determined values of refractive properties such as the focal length and the optical power. Typically, post-fabrication modification of refractive properties of lenses is difficult, cumbersome, and time consuming. Therefore, there is a great need for optical lenses whose refractive properties can be modified easily and efficiently post-fabrication, especially for highly sensitive medical applications. This requirement is even more critical in the case of intraocular lenses used in cataract surgery.

A number of efforts have been made in the past to fabricate optical lenses whose properties can be modified post-fabrication. Some examples include mechanical adjustment using motors, magnets, electrostriction or fluid pressure, and electro-optic adjustment using liquid crystalline materials. But clinically most suitable method is changing optical properties using light. Many intraocular lenses whose optical properties can be changed using light are disclosed in the prior art. Some of them comprise material compositions whose optical power can be changed to a desired value or locked in at a particular value by exposing to suitable doses of radiation. But there are many limitations associated with these lenses.

These lenses require doses of ultra violet light for power adjustment, which often exceed the safety limits established for retinal exposure. Therefore, a number of safety measures must be taken to avoid injury to the retina during lens power adjustment and, particularly, during lens power lock-in. As a result, highly trained staff must perform these post-operative procedures and the light delivery devices require sophisticated components and frequent calibration of the alignment and intensity of the light. In parts of the world where senile cataract is prevalent, there are relatively few highly trained staff relative to the size of the patient population, the cost of acquiring sophisticated equipment can be prohibitive, and specialized maintenance can be problematic. Therefore, it is desirable to have intraocular lenses whose refractive properties can be adjusted and locked-in using a safe dose of visible light, after the lens is fabricated.

Furthermore, light adjustable intraocular lenses of the prior art do not provide a visually observable indication that power adjustment and power lock-in have been performed. In resource poor settings, it is often very difficult for patients to return to the clinic for the power adjustment and power lock-in procedures. During follow up visits, healthcare providers may need to actively seek patients in rural settings, to provide adjustment and lock-in services. Therefore, it is desirable to have a colored intraocular lens that clearly indicates that a medical follow-up is pending.

Moreover, light adjustable lenses of the prior art require the patients to use protective eye wear, after the surgery, till the day the intraocular lens is locked in, in order to avoid exposure to sunlight. However, for patients returning to harsh living and working conditions, protective eyewear may get damaged and it may be difficult to obtain replacement protective eyewear. Therefore, it is highly desirable to have a colored intraocular lens that protects the eye and reduces the need for additional protective eye wear. In spite of the efforts reported in the prior art, there is a need for optical lenses whose optical properties can be changed using safe doses of visible light. Also there is a requirement for colored optical lenses that clearly indicate if their power has been changed and locked in. There is also a requirement for colored optical lenses that eliminates the need for eyewear protection after cataract surgery. There is also need for developing material compositions that are suitable for making colored optical lenses for nonmedical applications. U.S. Pat. No. 6,450,642 describes lenses capable of post-fabrication power modification. It describes a first composition comprising a polymer matrix and a second refraction modulating composition. The first composition is cross-linked in the presence of the second refraction modulating composition. Further as illustrated in the examples, the first composition and the second composition are necessarily based on siloxanes so that the two components are compatible with each other. According to the teaching of the patent it is desirable that the mechanism for cross-linking the first composition is different than the mechanism for the polymerization of the components of the refraction modulating composition. This necessitated functional modification of the siloxanes of the refraction modulating composition. Further this approach does not enable photobleaching, and the production of coloured intraocular lenses.

SUMMARY OF THE INVENTION

It has now been surprisingly found that many of the limitations in the synthesis and the performance of the photo-responsive shape changing polymer compositions, optical lenses and more particularly intraocular lenses fabricated there from can be overcome by preparing compositions comprising a cross-linked polymer matrix, then incorporating a polymerizable composition in the cross-linked polymer matrix and then polymerizing the polymerizable composition.

The present invention overcomes the limitations of the prior art by providing photo-responsive shape changing polymer compositions which can also be locked in by exposure to a dose of the visible light well within the established safety limits for retinal light exposure.

According to an embodiment of the invention, a photo-responsive shape changing polymer composition suitable for a colored optical lens is provided. The composition comprises: a photoinitiator that absorbs light in the wavelength range of about 400 nm to about 700 nm; a cross-linked polymer matrix; and a polymerizable composition wherein, exposing the photo-responsive shape changing polymer composition to a photobleaching dose of light, in the wavelength range of about 400 nm to about 700 nm, significantly photobleaches the said photo-responsive shape changing polymer composition.

In another embodiment, the present invention provides photo-responsive shape changing polymer compositions that resist photochemical reactions under conditions that correspond to bright outdoor sunlight, and thus reducing or even eliminating the need for protective eye wear in the postoperative period prior to change in shape, optical properties and lock-in of the polymer composition.

These and other features, aspects, and advantages of the present invention will be better understood when the following detailed description is read along with the accompanying drawings.

DETAILED DESCRIPTION OF THE INVENTION

Figure 1:
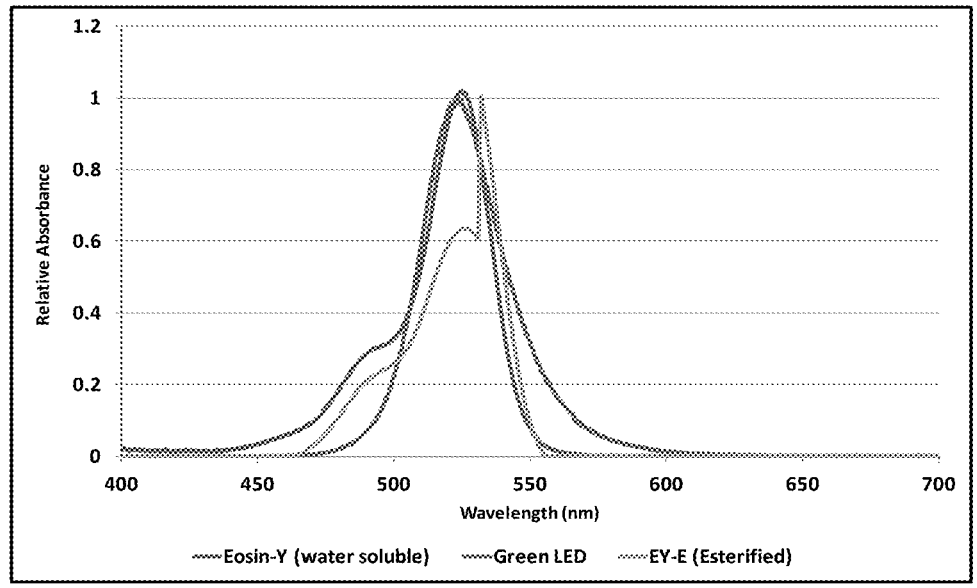
FIG. 1. Comparison of a typical absorption spectrum of Eosin-Y in water, esterified Eosin-Y dissolved in n-hexane along with the emission spectrum of a green LED.

The present invention relates generally to photo-responsive shape changing polymer compositions. Particularly, this invention relates to photo-responsive shape changing polymer compositions that can be reshaped by exposing to a dose of visible light. More particularly, the invention relates to photo-responsive shape changing polymer compositions that can be formed into a lens and reshaped by exposing the lens to a dose of visible light that is safe for exposure to the human eye. It also relates to intraocular lenses that can be photobleached and to colored intraocular lenses made from photo-responsive shape changing polymer composition and their method of use.

The term "photo-responsive shape change" refers to a change in the refractive properties of a shape changing polymer composition that occurs when the said composition is exposed to visible light in the range of about 400 nm to about 700 nm.

The photo-responsive shape change of the polymer compositions is manifest in the refractive characteristics of the polymer compositions, specifically optical lenses and more particularly intraocular lenses. The term "refractive properties" refers to the way the light is refracted through an optical lens and relates to terms, including the focal length, the dioptric power of the lens and wavefront, known to a skilled person. A person skilled in the art is familiar with the ways that gradients in the refractive index and the shape of the refracting surfaces of a lens, and the refractive index of the medium in which the lens is used, contribute to the refractive properties of a lens. A person skilled in the art is familiar with the characterization of refractive properties in terms of the sphere dioptric power, cylinder dioptric power, and orientation of the cylinder axis and understands that wavefront can be used to characterize the refractive properties of a lens.

The "medium in which the lens is used" is specified by the intended use. For example, in a camera, the lens is typically surrounded by air (with a refractive index that is very close to 1.00). In the human eye, an intraocular lens is typically surrounded by aqueous and vitreous fluids or clinical replacements for these.

The term "light" as used herein refers to light of wavelength in the range from about 400 nm to about 700 nm.

The term "colored" as used herein refers to a polymeric compositions that preferentially absorbs light over some portion of the visible spectrum giving the transmitted light a color corresponding to wavelengths that were not preferentially absorbed by the polymeric compositions.

The term "photobleaching" as used herein refers to the decrease in the peak absorption of visible light by photo-responsive shape changing polymer compositions when exposed to light that includes wavelengths that excite one or more of the chromophores in the photo-responsive shape changing polymer compositions.

The photo-responsive shape changing polymer composition comprises a) a photoinitiator that absorbs light in the wavelength range of about 400 nm to about 700 nm b) a cross-linked polymer matrix c) a polymerizable composition and optionally d) a hydrogen donor and e) an electron donor. The features of each of these are discussed in details below.

"Macromer" as used herein refers to an oligomer that has been functionalized as to contain more than one vinyl unsaturation.

"Lens" as used herein refers to an optical element that is capable of refracting light. In the context of the present description, a lens may be a window, a prism, a cylinder, a sphere, an element that has a planar surface or a curved surface.

"Photoinitiator" as used herein refers to a chemical species that absorbs light in the wavelength range of about 400 nm to about 700 nm and is capable of participating in a chemical reaction such that the absorption of light enhances the rate of the chemical reaction.

"Photopolymerization" as used herein refers to a polymerization reaction carried out in the presence of light wherein the rate of polymerization is greater than that in the absence of light, all other experimental conditions remaining the same.

The term "shape change dose" is the light dose (product of exposure intensity and exposure duration) absorbed by the photo-responsive shape changing polymer composition to achieve at least 1% photopolymerization of the polymerizable composition The term "significantly photobleached" implies the peak absorbance in the visible wavelength region is decreased by more than 50% from its original value For the purpose of the invention, the term "photobleaching dose of light" implies the light dose (product of exposure intensity and exposure time) capable of photobleaching the photoinitiator significantly so as to reduce the peak absorbance of light, in the wavelength range of about 400 nm to about 700 nm, to at least half of its original value.

The term "lock-in dose" is the light dose (product of exposure intensity and exposure time) absorbed by the photo-responsive shape changing polymer composition to photopolymerize more than 90% of polymerizable composition.

The term lower order aberrations refers to change in wavefront of light rays when they refract or reflect from an optical surface like a lens or a mirror. Lower order aberrations as represented by zernike polynomial representation are tip, tilt, defocus, vertical astigmatism and oblique astigmatism.

The term higher order aberrations refers to change in wavefront of light rays when they refract or reflect from an optical surface like a lens or a mirror. Higher order aberrations as represented by zernike polynomial representation are vertical coma, horizontal coma, vertical trefoil, oblique trefoil, primary spherical, vertical secondary astigmatism, oblique secondary astigmatism, oblique qudrafoil, vertical qudrafoil.

The photoinitiator selected absorbs light in the wavelength range of about 400 nm to about 700 nm. The color of the photo-responsive shape changing polymer composition is primarily governed by the choice of the photoinitiator. Depending upon the type of photoinitiator selected, it can initiate photopolymerization by generating radicals by 1) bond cleavage, 2) by transferring the energy to an electron or a hydrogen donor molecule. The first type of photoinitiators is called Type1 photoinitiators and the latter type is called Type 2 photoinitiators.

Typically, Type 2 photoinitiators require a co-initiator such as an electron donor, in order to initiate the photopolymerization reaction. In such situations the electron donor is incorporated in the cross-linked polymer matrix. The electron donor comprises a molecule selected from the group consisting of aliphatic or aromatic primary, secondary, tertiary amines, diphenyliodonium chloride salt, N phenyl glycine (NPGs), benzyltrimethylstannanes, thiols, arylsulfinates, sulfur compounds, 1,3-diketone enolates, phosphines, carboxylates, borates, organotins, and amino acids (in the presence of phenoxazines).

The choice of photoinitiators of the type 1 and type 2 and their details are discussed in chapters 8 and 9 of "Photoinitiators for Polymer Synthesis" by Jean Pierre Fouassier and Jacques Lalevee, Wiley 2012.

The cross-linked polymer matrix comprises monomers selected from the family of acrylate and methacrylate monomers.

The cross-linked polymer matrix comprises monomers selected from 2 ethyl hexyl acrylate, butyl acrylate, 2 ethyl hexyl methacrylate, isobutyl acrylate, and tertiary butyl acrylate, octyl acrylate, octyl methacrylate, decyl acrylate, decyl methacrylate, lauryl acrylate, lauryl methacrylate.

The cross-linked polymer matrix comprises cross-linkers.

The cross-linked polymer matrix comprises cross-linker selected from ethylene glycol dimethacrylate, hexane diol diacrylate, ED 20 acrylate, trimethylol propane triacrylate, dipentaerythrito hexa acrylate, glycerol triacrylate, hexanediol diacrylate.

The cross-linked polymer matrix comprises macromers. Various techniques of synthesis of acrylate and methacrylate macromers are described by Couthouis et al Macromol. Chem. Phys. (2015) Vol 216, 1791-1800; Haloi et al Journal of Polymer Science: Part A: Polymer Chemistry, Vol. 47, 6526-6533 (2009), Datta et al Journal of Polymer Science: Part A: Polymer Chemistry, Vol. 45, 1661-1669 (2007), Chan et al Macromol. Chem. Phys. 2008, 209, 1797-1805 (2008) and U.S. Pat. No. 7,763,688.

Polymerizable composition comprises a hydrophobic monomer selected from 2 ethyl hexyl acrylate, 2 ethyl hexyl methacrylate, decyl acrylate, decyl methacrylate, lauryl acrylate, lauryl methacrylate.

Polymerizable composition comprises a hydrophobic crosslinker selected from ethylene glycol dimethacrylate, hexane diol diacrylate, ED 20 acrylate, trimethylol propane triacrylate, dipentaerythritol hexa acrylate, glycerol triacrylate, hexanediol diacrylate.

Polymerizable composition comprises a macromer bearing multiple unsaturations. Various techniques of synthesis of acrylate and methacrylate macromers are described by Couthouis et al Macromol. Chem. Phys. (2015) Vol 216, 1791-1800; Haloi et al Journal of Polymer Science: Part A: Polymer Chemistry, Vol. 47, 6526-6533 (2009), Datta et al Journal of Polymer Science: Part A: Polymer Chemistry, Vol. 45, 1661-1669 (2007), Chan et al Macromol. Chem. Phys. 2008, 209, 1797-1805 (2008) and U.S. Pat. No. 7,763,688.

Polymerizable composition comprises a mixture of a) monomers and cross-linkers b) monomers and macromers c) cross-linkers and macromers or d) monomers, cross-linkers and macromers described above.

The hydrogen donor is selected from N phenyl glycine, benzyltrimethylstannanes, thiols, arylsulfinates, sulfur compounds, 1,3-diketone enolates, phosphines, carboxylates, borates, organotins, and amino acids (in the presence of phenoxazines), hydroxyl acrylates, hydroxyl methacrylates, ascorbic acid.

While hydrogen donors can be selected from a wide range of compounds described earlier, hydroxyl-acrylates used as monomers do also function as hydrogen donors.

In order to avoid unwanted photopolymerization, the reactive radicals generated by the photoinitiator must be captured before they can initiate photopolymerization. In the prior art, polymerization inhibitors are added to polymer compositions in order to capture the radicals before they can cause any polymerization. However, the amount of inhibitor needed depends upon the ambient light exposure of the eye. Calculating the amount of ambient light exposure requires finding out the daily routine of a patient, which is a difficult task. In order to avoid this, the prior art suggested adding typically a large amount of inhibitors. However increasing the amount of inhibitor would increase the light flux needed for shape adjustment and lock-in which might exceed the safety limits suitable for human eyes. The present invention overcomes these limitations by the choice of photoinitiators, electron donors and hydrogen donors.

The photo-responsive shape changing polymer compositions described herein are useful in a number of applications where it is desirable to change the properties of polymeric composition after it has been formed into a specific product. The compositions are useful in fabricating a wide array of optical elements such as spectacle lenses, mirrors, contact lenses, intraocular lenses, telescopic lenses, recordable media, such as compact disks, and the like. The said polymeric compositions are useful to form various types of implants where it is desirable to modify the shape or physical properties of the implant after it has been implanted.

The main advantage of the photo-responsive shape changing polymer compositions of the present invention is that their refractive properties can be modified post fabrication. The shape of polymer composition can be changed on exposure to visible light. For example, by exposing to a dose of light, in the wavelength range about 400 nm to about 700 nm, the shape of the polymer composition can be changed by inducing the photoinitiator to cause photopolymerization of the polymerizable composition. The shape of the photo-responsove shape changing polymer composition and hence the refractive properties can be changed, by exposing it to light in the visible wavelength range. Most of the light adjustable lenses, disclosed in the prior art, require doses of ultra violet light for power adjustment, which is exceed the safety limits established for retinal exposure. Further the shape change of polymer compositions and intraocular lenses made there from can be locked in by exposure to a safe dose of visible light.

According to an embodiment the present invention provides a photo-responsive shape changing polymer composition comprising: a) a photoinitiator that absorbs light in the wavelength range of about 400 nm to about 700 nm b) a cross-linked polymer matrix c) a polymerizable composition d) a hydrogen donor and e) an electron donor.

According to an embodiment the present invention provides a photo-responsive shape changing polymer composition wherein a) the photoinitiator c) the polymerizable composition d) the hydrogen donor and e) the electron donor are incorporated within the cross-linked polymer matrix b).

According to an embodiment of the present invention the polymerizable composition comprises a monomer M selected from 2 ethyl hexyl acrylare, 2 ethyl hexyl methacrylare, decyl acrylate, decyl methacrylate, lauryl acrylate, lauryl methacrylate According to an embodiment of the present invention the polymerizable composition comprises a crosslinker $C_x$ selected from 1) tri methylol propane triacrylate (TMPTA-CAS-15625-89-5), dipentaerythritol hexa acrylate (DPHA, CAS-60506-81-2), glycerol tri acrylate (GTA, CAS-5459-38-1), hexanediol diacrylate (HDDA, CAS-13048-33-4)

According to an embodiment of the present invention the polymerizable composition comprises a macromer.

According to an embodiment of the present invention the polymerizable composition comprises a macromer selected from Ma1 and Ma2, described in examples 6A and 6B.

According to an embodiment of the present invention the polymerizable composition comprises a mixture of a monomer and a crosslinker.

According to an embodiment of the present invention the polymerizable composition comprises a mixture of a monomer and a macromer.

According to an embodiment of the present invention the polymerizable composition comprises a mixture of a crosslinker and a macromer According to an embodiment of the present invention the polymerizable composition comprises a mixture of a monomer, crosslinker and a macromer In an embodiment of the invention, the photoinitiator composition comprises a molecule which absorbs light in the wavelength range of about 400 nm to about 700 nm and is capable of participating in a chemical reaction such that absorption of light enhances the rate of the chemical reaction.

According to an embodiment of the invention, the photoinitiator can be Type1 photoinitiator.

According to an embodiment of the invention, the photoinitiator can be Type2 photoinitiator.

According to another embodiment of the invention, a combination of photoinitiators is used as to obtain the absorption spectrum in the range of about 400 nm to about 700 nm.

According to another embodiment of the invention the components of the photoinitiator composition are soluble in the cross-linked polymer matrix.

According to another embodiment of the invention the photoinitiator molecule is chemically modified in order to enhance solubility in the composition selected to form cross-linked polymer matrix.

According to another embodiment of the invention the photoinitiator is modified by covalently attaching a hydrophobic alkyl chain to the photoinitiator molecule.

According to another embodiment of the invention the photoinitiator could either be dispersed, or covalently attached to the polymer matrix or to the macromer or to both.

According to an embodiment of the present invention are provided photoinitiator compositions which have a threshold limit, below which there is no photopolymerization. The threshold intensity is 0.5 mw/cm$^2$ of green light spectrum as shown in FIG. 1.

According to a preferred embodiment of the present invention, the photoinitiator comprises a Eosin-Y derivative.

According to a more preferred embodiment of the present invention, the photoinitiator comprises a 2ethyl hexyl ester of Eosin-Y.

According to an embodiment of the invention the photoinitiator is present in the concentration range of about 0.01% to 1% wt by wt of photo-responsive shape changing polymer composition In another embodiment of the invention the photo-responsive shape changing polymer compositions further comprise photoinitiator, electron donors and hydrogen donors, outside the cross-linked polymer matrix.

According to another embodiment of the invention the electron donor is present in concentration range 0.01-10% wt by wt of the photo-responsive shape changing polymer composition According to another embodiment of the invention a combination of electron donor molecules is used.

In another embodiment of the invention the electron donor is selected from aliphatic amines such as dimethyl amino ethyl methacrylate, dimethyl amino ethyl acrylate.

In a preferred embodiment of the present invention, the electron donor comprises dimethyl amino ethyl acrylate in concentration range 0.01-10% wt by wt of the photo-responsive shape changing polymer composition According to an embodiment of the present invention the hydrogen donor is present in concentrations ranging from 0.001%-10% wt by wt of the photo-responsive shape changing polymer composition.

According to an embodiment of the present invention the hydrogen donor is preferentially partitioned within the photo-responsive shape changing polymer composition so as to bring about photobleaching without influencing the mechanical, refractive and thermal properties of the photo-responsive shape changing polymer composition.

According to an embodiment of the present invention a combination of hydrogen donor molecules is used. The hydrogen donor molecule is dispersed or is covalently attached to the matrix or to the macromer or a combination of both.

In an embodiment of the invention, the hydrogen donor comprises citric acid

In an embodiment of the invention, the hydrogen donor comprises citric acid derivatives selected from citric acid esters, citric acid amides In another embodiment of the invention, the hydrogen donor comprises hydroxyl-acrylates.

In another embodiment of the invention the concentration of hydroxyl acrylates is in the range 0.001 to 0.0.10% wt by wt of the photo-responsive shape changing polymer composition.

According to an embodiment of the present invention, the cross-linked polymer matrix has a glass transition temperature in the range −70° C. to 10° C.

According to an embodiment of the invention, the photo-responsive shape changing polymer composition comprises a cross-linked polymer matrix in which the polymerizable composition is sorbed.

According to an embodiment of the invention the diffusivity of the polymerizable composition in the polymer matrix is in the range $10^{-2}$ mm$^2$/sec to $10^{-7}$ mm$^2$/sec, and the polymerizable composition is preferentially partitioned within the cross-linked polymer matrix.

According to an embodiment of the invention the cross-linked polymer matrix comprises a polyacrylate.

According to an embodiment of the invention the cross-linked polymer matrix comprises a polymethacrylate.

According to an embodiment of the invention the cross-linked polymer matrix is cross-linked by a cross-linker According to an embodiment of the invention the cross-linked polymer matrix is cross-linked by a macromer.

According to an embodiment of the invention the photo-responsive shape changing polymer compositions that are useful for optical lenses comprise a polymerizable composition and cross-linked polymer matrix such that diffusivity of the former in the latter is in the range of $10^{-4}$ mm$^2$/sec to $10^{-7}$ mm$^2$/s at 25° and equilibrium swelling at 25° C. in the range 100% to 1000% weight by weight.

According to an embodiment of the present invention are disclosed photo-responsive shape changing polymer compositions that enable a broad range of the precisely controlled shape changes and changes in refractive properties.

According to an embodiment of the present invention the shape change may be done multiple times.

According to an embodiment of the present invention, after the shape change is achieved, the photo-responsive shape changing polymer composition is exposed to a lock-in dose of light which prevents unintentional change of shape on exposure to light.

According to an embodiment of the present invention the lock-in dose is in the range 100 milli joules/cm$^2$ to 50 joules/cm$^2$ According to an embodiment of the present invention, the composition of the photo-responsive shape changing polymer composition is so chosen that it can be significantly photobleached at safe light intensity levels.

In an embodiment of the present invention the photobleaching dose of light is substantially greater than the shape change dose of light.

In a preferred embodiment of the present invention the photobleaching dose of the photo-responsive shape changing polymer composition is 1.5 to 20 times its shape change dose.

In an embodiment of the present invention, the photobleaching dose of the photo-responsive shape changing polymer composition is substantially same as the lock-in dose of the photo-responsive shape changing polymer composition.

In an embodiment of the present invention, the photo-responsive shape changing polymer compositions of the present invention are shaped in the form of an optical lens., which is accomplished by using a mold and methods typically used for making polymeric lenses.

In an embodiment of the present invention, the photo-responsive shape changing polymer compositions of the present invention are shaped in the form of an intraocular lens which is accomplished by using a mold and methods typically used for making polymeric lenses According to an embodiment of the present invention the photo-responsive shape changing polymer compositions are used to make colored intraocular lenses.

According to an embodiment of the present invention intraocular lenses made from photo-responsive shape changing polymer compositions exhibit photoresponsive refractive properties.

According to an embodiment of the present invention, when the photo-responsive shape changing polymer composition is used in the fabrication of the intraocular lenses, the same exhibits more than 70% cell viability during in vitro cytotoxicity test by direct contact method as per ISO 10993-6

According to an embodiment of the present invention for applications of the photo-responsive shape changing polymer compositions as intraocular lenses, the electron donor is present in the range 0.01 to 10% wt by wt. of the lens.

According to another embodiment of the present invention the electron donor is preferentially partitioned within the photo-responsive shape changing polymer composition provides an optically clear composition, and does not alter the mechanical, optical and the thermal properties of the shape changing polymer composition.

According to another embodiment of the invention for applications of the shape changing polymer composition as intraocular lens, the said polymer composition does not photopolymerize or photobleach under ambient light conditions such as in a well lit room, watching television, working in the field etc.

According to an embodiment of the present invention, the power of the intraocular lens made from the photo-responsive shape changing polymer composition, can be changed easily after inserting the lens into the eye by simply exposing it to a shape change dose of visible light in the wavelength range of about 400 nm to about 700 nm.

In an embodiment of the present invention, photo-responsive shape changing polymer compositions suitable for colored optical lens are provided.

According to an embodiment of the present invention, when the photo-responsive shape changing polymer compositions are used for making colored intraocular lenses to be used after the cataract surgery, the colored optical lenses clearly indicates the status of lock-in.

According to an embodiment of the present invention, the coloured intraocular lenses made from the photo-responsive shape changing polymer compositions, when photobleached, protect the eye from harmful UV radiation.

In yet another embodiment of the invention are provided colored intraocular lenses.

Yet another aspect of the present invention is to provide a method of implementing a colored intraocular lens made of a photo-responsive shape changing polymer composition, and implanting the same within the eye, comprising: (a) exposing at least a portion of the colored intraocular lens to a shape changing dose of light, in the wavelength range of about 400 nm to about 700 nm, so as to change the shape of the lens (b) exposing at least a portion of the colored intraocular lens to a lock-in dose of light, in the wavelength range of about 400 nm to about 700 nm, so as to lock the shape of the lens and prevent further substantial change in shape as manifested in the refractive properties; (c) exposing at least a portion of the colored intraocular lens to a photobleaching dose of light, in the wavelength range of about 400 nm to about 700 nm, as to photobleach the photoinitiator significantly; and (d) producing a significantly photobleached locked in intraocular lens.

The invention is further described by following examples which are offered by way of illustration only and are not intended to limit the scope of the invention in any manner.

Example 1: Preparation of Modified Eosin-Y Photoinitiator

Eosin-Y (MERCK, CAS no. 17372-87-1) is insoluble in hydrophobic acrylate monomers. A hydrophobic chain was attached to Eosin-Y via an esterification reaction to make Eosin-Y soluble in hydrophobic acrylate monomers. In a 250 mL round bottom flask, 5.0 g of Eosin-Y was added in 100 mL Toluene. 10 g of Amberlyst-15-hydrogen form macroporous beads (Sigma-Aldrich, CAS no. 39389-20-3) were added. The flask was immersed in an oil bath maintained at 70° C. and stirred intermittently (once in 10 min) overnight using magnetic stirring bar. Then, 11.35 mL 2-ethyl hexane-1-ol (SD Fine chemicals; CAS no. 104-76-7) was added and a clean dean and stark apparatus was attached to the round bottom flask. The temperature of the reaction mixture was raised to 120° C. The reaction mixture was stirred intermittently once in 10 min and maintained at 120° C. for 36 hours. Amberlyst-15 and unreacted Eosin Y were removed by filtration using Whatman filter paper no 1. Toluene was removed by evaporation on a rotary evaporator. The reddish brown mixture obtained was purified by washing with cold n-hexane (30 ml×3 times).

The product was further purified by dissolving it in 60 ml dichloromethane and the impurities were filtered over filter paper and dichloromethane was removed by evaporation on a rotary evaporator. The resulting product was further dried in a high vacuum desiccator to obtain fluffy reddish brown dry powder. It was observed that purified product was completely soluble in acrylate monomers and did not leave behind any residues.

FIG. 1 shows the comparison of absorption spectrum of Eosin-Y in water, esterified Eosin-Y (EYE) dissolved in n-hexane along with the emission spectrum of a green LED.

Example 2: Preparation of Cross-Linked Polymer Matrix Samples S1-S10

Monomer M1, monomer M2, monomer M3, crosslinker $C_x$, electron donor E1, hydrogen donor H1, esterified Eosin-Y (as prepared by the method described in example 1), thermal initiator R1 were mixed together in the ratios given in Table 1. The mixture was poured in a mold made using two flat glass plates separated by a Teflon spacer 1 mm in thickness. The assembly was kept in a hot air oven at 70° C. overnight. The resulting cross-linked matrix was taken out and cut into pieces of approximately 5 mm×5 mm×1 mm(l×b×h) in size.

TABLE 1

Synthesis of cross-linked polymer matrices S1-S17

| No | M1 % | M2 % | M3 % | $C_x$ % | EYE % | R1 % | E1 % | H1 % |
|---|---|---|---|---|---|---|---|---|
| S1 | EHA 89.7 | EHMA 9 | — | EGDMA 0.4 | 0.02 | 0.4 | DMAEMA 0.5 | — |
| S2 | EHA 98.2 | — | — | HDDA 0.3 | 0.02 | 0.4 | DMAEMA 1 | — |
| S3 | EHA 97.3 | — | — | HDDA 0.3 | 0.02 | 0.4 | DMAEMA 1 | HEA 1 |
| S4 | EHA 98.6 | — | — | HDDA 0.5 | 0.02 | 0.4 | DMAEMA 0.5 | — |
| S5 | EHA 99.0 | — | — | HDDA 0.1 | 0.02 | 0.4 | DMAEMA 0.5 | — |
| S6 | BA 98.8 | — | — | HDDA 0.25 | 0.02 | 0.4 | DMAEMA 0.5 | — |
| S7 | BA 98.8 | — | — | ED-20 acrylate* 0.25 | 0.02 | 0.4 | DMAEMA 0.5 | — |
| S8 | BA 99.0 | — | — | HDDA 0.1 | 0.02 | 0.4 | DMAEMA 0.5 | — |
| S9 | EHA 59.5 | BA 39.1 | — | HDDA 0.4 | 0.02 | 0.4 | DMAEA 0.5 | — |
| S10 | BA 33 | I-BA 33 | t-BA 33 | HDDA 0.1 | 0.02 | 0.4 | DMAEMA 0.5 | — |
| S11 | OA 99 | — | — | HDDA 0.1 | 0.02 | 0.4 | DMAEMA 0.5 | — |
| S12 | EHA 33 | I-BA 33 | OA 32.8 | HDDA 0.25 | 0.02 | 0.4 | DMAEMA 0.5 | — |
| S13 | EHA 58.0 | BA 38.3 | — | M6 2.5 | 0.04 | 0.4 | DMAEA 0.75 | — |
| S14 | EHA 59.5 | BA 39.1 | — | HDDA 4 | 0.04 | 0.4 | DMAEA 0.75 | — |
| S15 | EHA 59.5 | BA 39.1 | — | HDDA 4 | 0.06 | 0.1 | DMAEA 0.75 | — |

TABLE 1-continued

Synthesis of cross-linked polymer matrices S1 -S17

| No | M1 % | M2 % | M3 % | $C_x$ % | EYE % | R1 % | E1 % | H1 % |
|---|---|---|---|---|---|---|---|---|
| S16 | EHA 59.5 | BA 39.1 | — | HDDA 4 | 0.06 | 0.1 | DMAEA 0.75 | Ascorbic acid 0.01% by wt |
| S17 | EHMA 99 | — | — | HDDA 0.4 | 0.04 | 0.4 | DMAEMA 0.75 | — |

Wherein,
EHA: Ethyl hexyl Acrylate;
BA—Butyl acrylate;
EHMA—Ethyl hexyl methacrylate;
EGDMA—Ethylene glycol dimethacrylate;
HDDA—Hexanediol diacrylate;
DMAEMA—Dimethylaminoethyl methacrylate;
OA—Mixture of linear and branched chain isomers of octyl acrylate,
DMAEA—Dimethyl amino ethyl acrylate ,
EYE—Esterified Eosin-Y,
R1—Luperox 26

Figure 2:
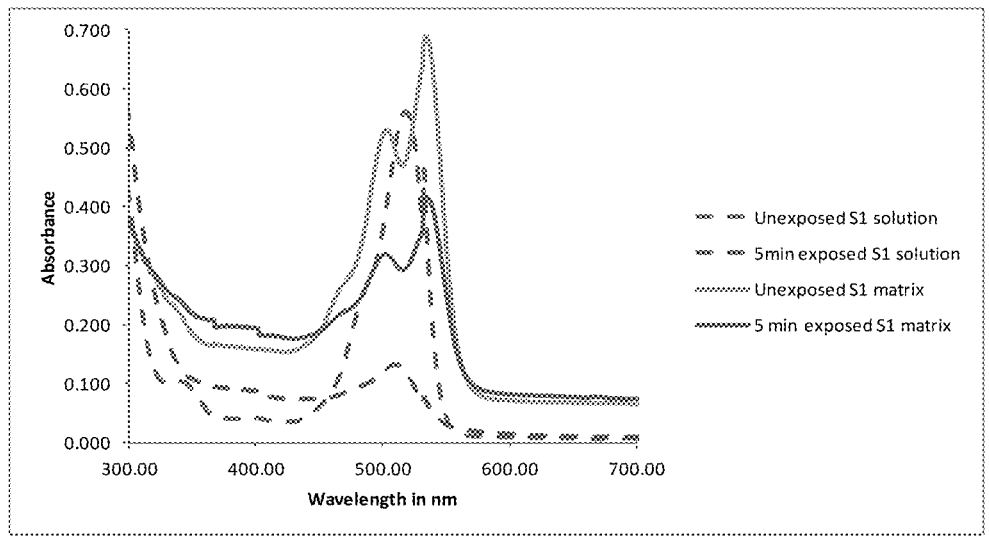
FIG. 2. Comparison of photobleaching in composition S1 of hydrophobic acrylate monomers vs composition S1 in cross-linked polymer matrix form.

Example 3 Comparison of Photobleaching Characteristics of a Composition in Solution Vs in the Cross-Linked Polymer Matrix Compositions S1 in solution and as a cross-linked polymer matrix made by polymerizing the same composition were separately exposed to a green light of intensity 8 mw/cm² for duration of 5 minutes. FIG. 2 shows that the photobleaching in the cross-linked polymer matrix requires much higher light dose to achieve the same percentage of photobleaching compared to that in the solution form.

Figure 3:
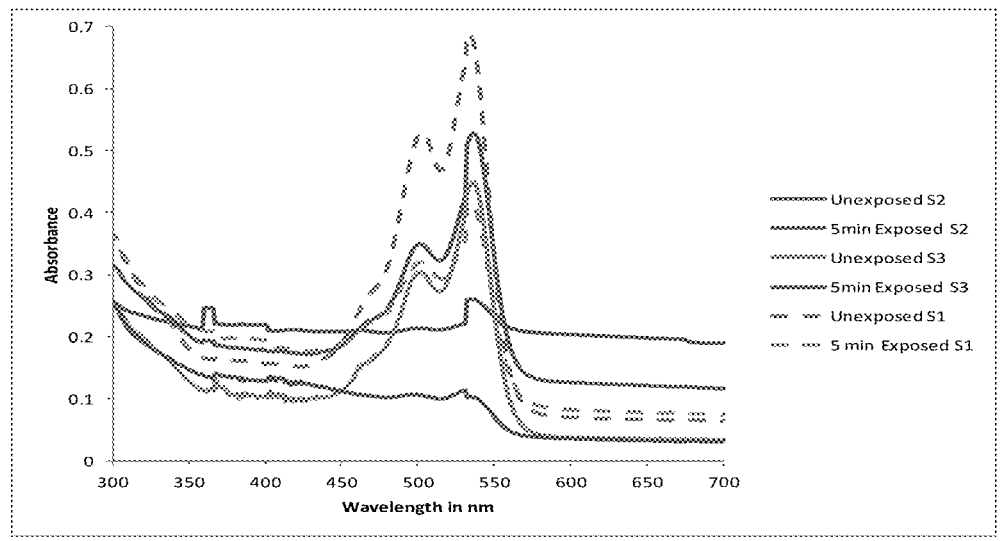
FIG. 3: Comparison of absorbance spectra of cross-linked polymer matrices of compositions S1, S2, and S3 before and after exposure to identical dose of light.

Example 4 Comparison of Photobleaching Characteristics of Cross-Linked Polymer Matrices Cross-linked polymer matrices made using compositions S1, S2 and S3 were exposed to green light with an intensity of 8 mw/cm² for 5 minutes. FIG. 3 shows that the photobleaching in cross-linked polymer matrices made from compositions S2 and S3 is higher as compared to cross-linked polymer matrix made using composition S1. The figure clearly shows that photobleaching characterized by percent decrease in the peak absorbance is in the order S3>S2>S1. Photobleaching dose in the cross-linked polymer matrix can thus be changed by changing the composition.

Example 5 Mechanical Properties of Cross-Linked Polymer Matrix

Figure 4:
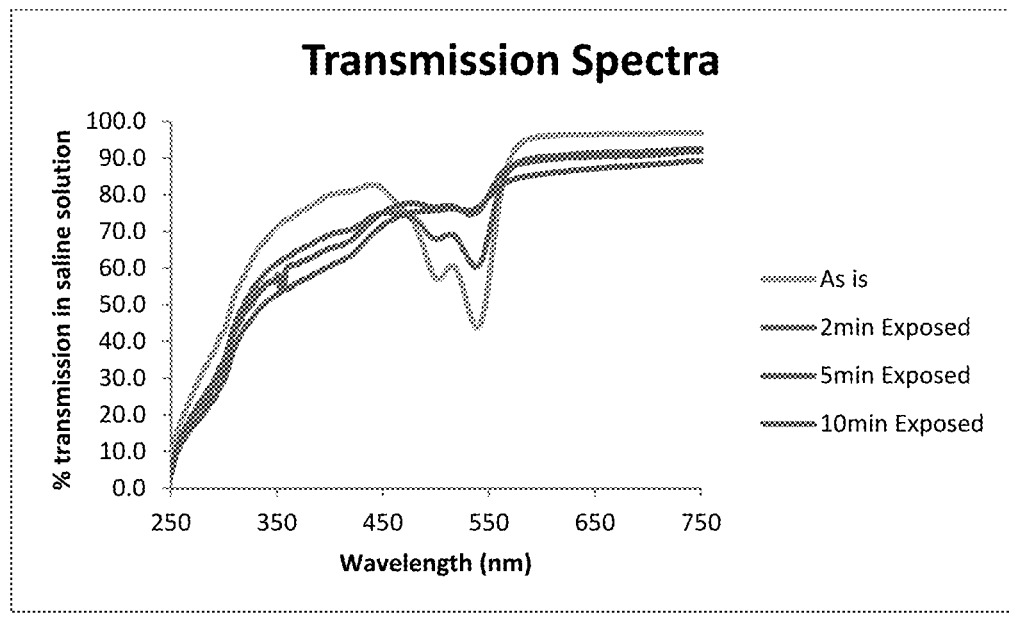
FIG. 4: Tensile strength test i.e. load vs elongation using a DMA (dynamic mechanical analyzer) for cross-linked polymer matrices S4, S5, S6 and S7.

Mechanical properties of cross-linked polymer matrices made from compositions S4, S5, S6 and S7 were measured using a dynamic mechanical analyzer. FIG. 4 shows that in sample S6 and S7 both made from butyl acrylate, changing the type of crosslinker changed the slope of the curve i.e. the Young's modulus. Similarly, in S4 and S5 samples, changing the crosslinker density changed the break-point of the matrix.

Example 6 Preparation of Macromers

Example 6 a Synthesis of Macromer Ma1

Macromer Ma1 was prepared by the method given below. Chemicals used; 2-ethylhexyl acrylate: 8.0 g; 4-Hydroxybutylacrylate: 0.698 g; Luperox-26: 2.03 g MEK (Methyl ethyl ketone)

The reaction was performed in a cylindrical vessel of internal diameter 55 mm with a port to purge nitrogen. The agitator used was a 6 bladed Ruston turbine having a 24 mm diameter. 8.0 g 2-ethylhexyl acrylate and 0.698 g hydroxybutyl acylate were added in 100 mL Methyl ethyl ketone and poured into the cylindrical reaction vessel. The reaction vessel was then maintained at 75° C. using a preheated oil bath. The solution was blanketed with Nitrogen and Luperox-26 (2.08 g) in 10 mL Methyl ethyl ketone was added. Further, the reaction mixture was stirred using overhead stirrer (REMI RQ-20) at a stirring rate of 300 rpm at 75° C. for 3.0 h. The blades of the turbine were positioned at $⅓^{rd}$ height of the total reaction mixture in the reaction vessel. After 3.0 h, solvent (Methyl ethyl ketone) was removed by evaporation on a rotary evaporator at 75° C. and vacuum 650 Torr. To remove Luperox-26, the oligomer was washed using dimethyl sulphoxide. Luperox-26 is soluble in dimethyl sulphoxide and oligomer is insoluble. DMSO (50 mL) was added to oligomer in round bottom flask (100 mL). Flask was shaken for 10 min and set aside for an hour. The mixture was then poured into separating funnel and allowed to stand for 30 min to separate both layers. Dimethyl sulphoxide layer was separated and discarded. In oligomer layer, 60 mL of n-hexane was added to dissolve the oligomers. The n-hexane layer was washed with distilled water (DW) (80 mL×3 times) to remove residual DMSO. N-hexane layer was separated and dried on sodium sulphate. N-hexane was removed by evaporation on a rotary evaporator at 70° C. and a clear viscous liquid was obtained.

Esterification of the Oligomer

The oligomer was esterified using acryloyl chloride: Oligomer: 7.62 g, Acryloyl chloride: 0.52 mL Triethyl amine (TEA): 1.01 mL Dichloromethane (DCM): 50 ml The reaction was performed in a 100 mL round bottom flask. Oligomer (7.62 g) was dissolved in 40 mL of dry DCM (Finar Chemicals). 1.0 mL TEA was added. The reaction mixture was kept in the dark in an ice bath maintaining temperature between 0 to 5° C. and stirring with magnetic bar (300 rpm). Acryloyl chloride (0.667 mL in 10 mL DCM) was added drop-wise using a dropping funnel over about 30 min and reaction mixture was maintained between 0 to 5° C. in ice bath under nitrogen atmosphere. The reaction mixture was stirred continuously for further 18 h in the dark under nitrogen atmosphere at room temperature. DCM was removed by evaporation on a rotary evaporator maintaining water bath at 40° C. and vacuum at 500 to 550 Torr. After DCM removal, the macromer was dissolved in n-hexane (70 mL) and washed thrice with saline water (0.9% NaCl solution (80 mL×3 times). N-hexane layer was separated and dried on sodium sulphate for about 1 hour. N-hexane layer separated was removed by evaporation on a rotary evaporator to yield macromer. Macromer was dried in desiccator using 4A molecular sieves, overnight at 4° C. in dark, whereupon a clear slightly yellowish liquid was obtained.

Example 6B: Synthesis of Macromer Ma2

Butyl acrylate (BA): 7.16 g, Hydroxyethyl methacrylate (HEMA): 1.82 g, Cuprous Bromide (CuBr): 0.429 g, Pentamethyl diethylenetriamine (PMDETA): 1.126 g, Ethyl-2 bromo propionate (EBP): 0.597 g, Methyl isobutyl ketone (MIBK) as solvent: 10 ml The reaction was performed in a 50 mL two neck round bottom flask under nitrogen blanket. BA and HEMA were weighed in round bottom flask and nitrogen gas was purged for 50 min. Then, quantities of MIBK; CuBr; PMDETA and ethyl-2 bromo propionate mentioned above were added. To remove dissolved oxygen the reaction vessel was purged three times using nitrogen gas and vacuum pump. Then the reaction vessel was immersed in preheated oil bath of 90° C. and stirred using magnetic bar under nitrogen atmosphere for 3 hrs. The reaction mixture was diluted with 120 ml DCM and the mixture was taken into separating funnel. DCM layer was then washed using EDTA solution (80 mL×4 times) and then with Distilled water (80 mL×3 times). DCM layer was separated and dried over anhydrous sodium sulphate for 1.0 hr. DCM was removed by evaporation on a rotary evaporator at 40° C. to isolate the oligomer.

Esterification of the Oligomer

The reaction was performed in a 100 mL round bottom flask (RBF). Oligomer (7.0 g) was dissolved in 40 mL dry DCM (Finar Chemicals) in 100 mL RBF. 2.57 mL of TEA (TCI) were added. The reaction mixture was kept in the dark in ice bath maintaining temperature in the range 0 to 5° C. and stirring with magnetic bar at 300 rpm. Acryloyl chloride (1.3 mL in 10 mL DCM) was added drop-wise using a dropping funnel for about 30 min and reaction mixture was maintained between 0 to 5° C. in ice bath under nitrogen atmosphere. The reaction mixture was stirred continuously for further 18 h in the dark under nitrogen atmosphere at room temperature. Solvent DCM was removed by evaporation on a rotary evaporator maintaining temperature of water bath at 40° C. and vacuum at 500 to 550 Torr. The macromer was dissolved in n-hexane (70 mL) and washed thrice with saline water (0.9% NaCl solution (80 mL×3 times). N-hexane layer was separated and dried on sodium sulphate for about 1 h. N-hexane layer was removed by evaporation on a rotary evaporator to yield macromer. Macromer was dried in desiccator using 4A molecular sieves overnight at 4° C. in the dark. The macromer was further purified by passing it through a basic alumina column.

Example 6 C Swelling of Cross-Linked Rpolymer Matrix in Polymerizable Composition and Diffusivity of Polymerizable Composition in Cross-Linked Polymer Matrix The cross-linked polymer matrices synthesized as per compositions in Table 1 were soaked in polymerizable compositions listed in table 2 and the equilibrium swelling of the polymer matrix in polymerizable composition was determined by noting the difference in weight before and after sorption. The diffusivity of polymerizable composition in the cross-linked polymer matrix was determined by measuring sorption of polymerizable composition as function of time and plotting amount sorbed as a function of square root of time. The results are summarized in Table 2 below.

TABLE 2

Diffusivity and equilibrium swelling of P2 in P1

| S. N | P1 | P2 | ES % | Mn (PD) | D × 10$^6$ |
|---|---|---|---|---|---|
| 1 | S5 | TMPTA | 23 | 296.3, (1.0) | 3.8 |
| 2 | S8 | DPEHA | 40 | 578.5, (1.0) | 3.0 |
| 3 | S9 | GTA | 71 | 254.2, (1.0) | 2.4 |
| 4 | S5 | HDDA | 98 | 226.27, (1.0) | 31 |
| 5 | S8 | HDDA | 629 | 226.27, (1.0) | 9.8 |
| 6 | S10 | HDDA | 559 | 226.27, (1.0) | 8.3 |
| 7 | S11 | HDDA | 232 | 226.27, (1.0) | 12 |
| 8 | S12 | HDDA | 202 | 226.27, (1.0) | 21.3 |
| 9 | S9 | Ma1 | 98 | 3250, (2.2) | 7.2 |
| 10 | S9 | Ma2 | 170 | 1700, (1.2) | 1.7 |
| 11 | S3 | 2-EHA | 1000 | 184.28 | 230 |

P1—cross-linked polymer matrix
P2—polymerizable composition
ES—Equilibrium swelling (by % change in weight after macromer uptake)
Mn—Number average molecular weight,
PD—Polydispersity index,
D—Diffusivity of polymerizable composition in the cross-linked polymer matrix (mm$^2$/sec)

Example 7 Sorption of Macromers in Cross-Linked Polymer Matrix

Figure 5:
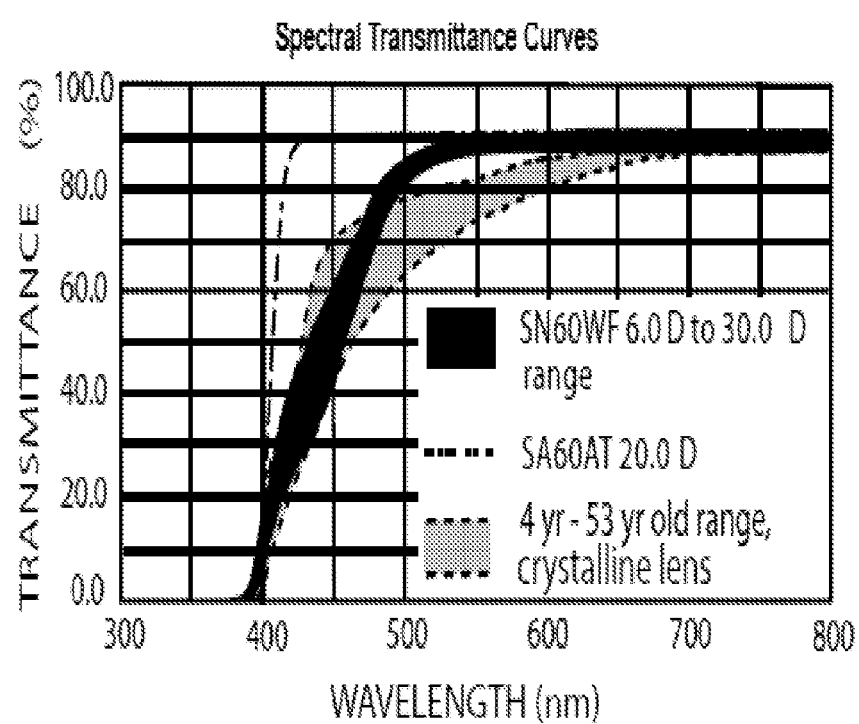
FIG. 5: Percent photopolymerization as a function of duration of exposure to light.

Macromer Ma1 was sorbed in 15 samples of cross-linked polymer matrix S9. The increase in weight was about 40%. The sorbed cross-linked polymer matrix was then exposed to light dose of green light of intensity 3 mw/cm$^2$ for varying durations. Each exposure duration was repeated three times. The amount of macromer photopolymerized was estimated by exhaustively extracting the unreacted macromer in n-hexane. The increase in weight of cross-linked polymer matrix gave the amount of macromer photopolymerized. FIG. 5 shows that the percentage of sorbed macromer photopolymerized on light exposure increases linearly with the light dose.

Figure 6:
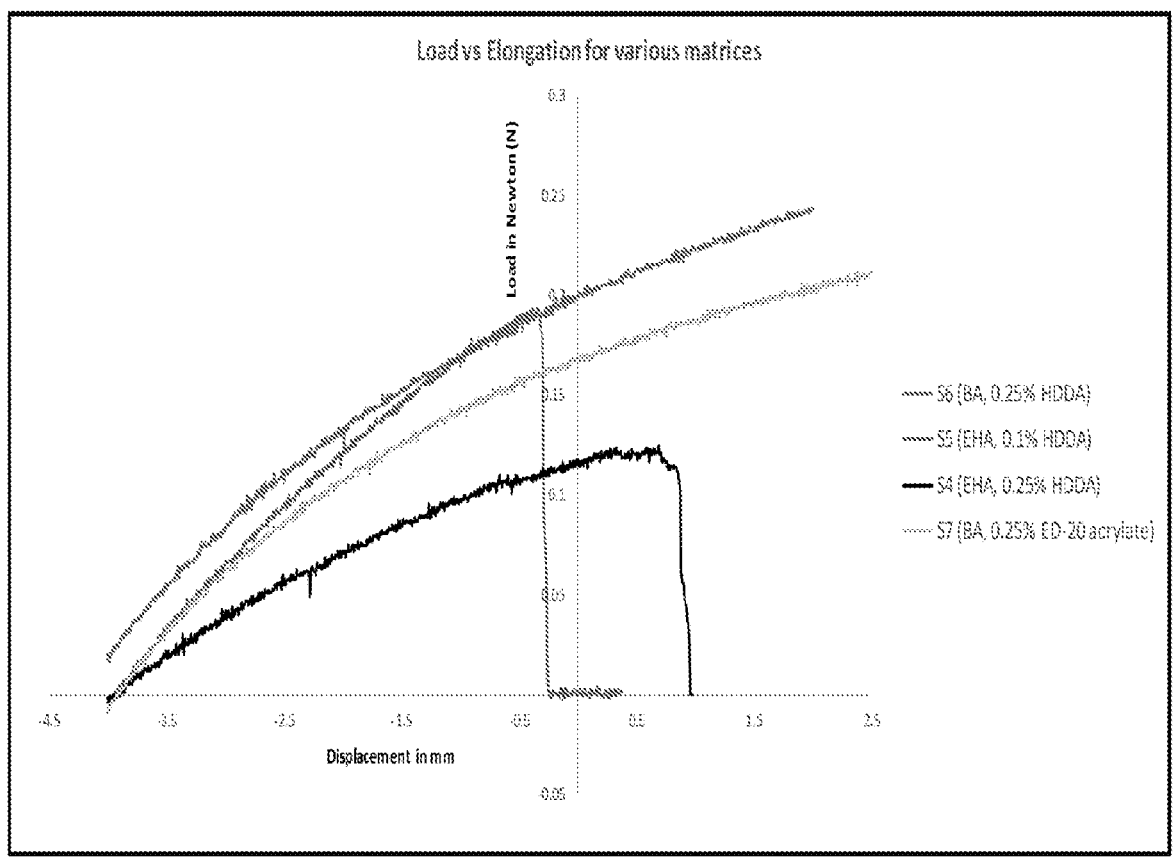
FIG. 6: Comparison of absorption spectra of cross-linked polymer matrices PB1, PB2 and PB3 before and after exposure to photobleaching dose of light.

Example 8 Photobleaching and Lock-in of Photo-Responsive Shape Changing Polymer Composition Four cross-linked polymer matrices were made by polymerizing the composition S14 and two cross-linked polymer matrices made by polymerizing composition S9. Hexane diol diacrylate HDDA, and macromer Ma2 were sorbed as described in table 3. The absorption spectra of the samples were measured in isotonic solution using a UV-Vis spectrophotometer. The samples were then exposed to photobleaching dose of light. After exposure the absorption spectrum was recorded again. Table 3 shows the peak absorbance before and after exposure. This example shows photobleaching in a photo-responsive shape changing polymer composition. (see FIG. 6)

TABLE 3

Change in peak absorbance of a matrix macromer pair before and after exposure.

| | | | | % sorption | Peak absorbance (538 nm) | | % peak absorbance |
|---|---|---|---|---|---|---|---|
| S.N | Sample | P1 | P2 | by weight | before exposure | after exposure | (538 nm) reduction |
| 1 | PB1 | S14 | HDDA | 40 | 2.008 | 0.2035 | 90 |
| 2 | PB2 | S14 | Ma2 | 35 | 1.921 | 0.071 | 96 |
| 3 | PB3 | S9 | HDDA | 40 | 0.65 | 0.11 | 83 |

Two samples of cross-linked polymer matrix S9 were made and HDDA was sorbed therein. Absorbance spectra of both samples in isotonic solution were recorded. One sample was exposed to photobleaching dose of light while other was used as control. Absorption spectrum was recorded after exposure to photobleaching dose of light. Both samples were then exhaustively extracted in Methyl ethyl ketone (MEK) to extract unpolymerized HDDA. The change in weight from initial unsorbed weight gives the amount of HDDA photopolymerized. The table below shows that the lens has photobleached before it has locked in. This shows that photobleaching dose of light is lower that lock-in dose.

TABLE 4

Photobleaching vs photopolymerization for various ratios of additives

| S.N. | P1 weight (mg) | P2 | Sorbed weight (mg) | Exposure intensity (mw/cm$^2$) | Exposure duration (mins) | % of HDDA polymerized | % reduction in peak absorbance |
|---|---|---|---|---|---|---|---|
| 1 | 61 | HDDA | 85.7 | 10 | 10 | 18% | 83% |
| 2 | 56 | HDDA | 84 | control | control | Less than 1% | 0% |

Above experiment was repeated using cross-linked polymer matrix made from composition S14 and macromer Ma2. Table 5 shows that the lens has been locked as well as photobleached. This shows that by changing the ratio of additives in the matrix the photobleaching dose of light can be altered and made comparable to lock-in dose of light.

TABLE 5

The amount of macromer polymerized for various samples.

| S.N. | Matrix weight (mg) | Macromer | Sorbed weight (mg) | Exposure intensity (mw/cm2) | Exposure duration (mins | % of macromer polymerized | % reduction in peak absorbance |
|---|---|---|---|---|---|---|---|
| 1 | 20 | Ma2 | 40.1 | 10 | 10 | 96% | 87% |
| 2 | 20 | Ma2 | 40.1 | control | control | 0% | 0% |

Example 9 Glass Transition Temperature Measurements

Four samples of cross-linked polymer matrix S14 and two samples of cross-linked polymer matrix S17 were prepared and were divided in three batches of two each. Glass transition temperature of the six samples was measured as per the protocol below.

7-10 mg of a film was cut and put in an aluminium DSC pan. The film was first heated to 100° C. at the rate of 20° C./min to remove thermal memory as well as any adsorbed water. The sample was then held isothermally at 100° C. for two minutes. The sample was then rapidly cooled at 40° C./min until it reached −50° C. The sample was then held isothermally at −50° C. for two minutes. The sample was then heated till 50° C. at 20° C./min. During the entire cycle nitrogen gas was purged and the same flow rate was maintained throughout.

Another batch of four sample of cross-linked polymer matrix S14 was prepared. HDDA was sorbed in cross-linked polymer matrix S14 to attain a sorption of 20% by weight and in the other set 50% sorption by weight was attained. These samples were then exposed to lock-in dose of light which polymerized more than 90% of the polymerizable composition in the sample. The samples were then exhaustively extracted in Methyl ethyl ketone (MEK) and dried overnight in a hot air oven. The glass transition temperatures of the samples were measured using the above protocol and are reported in table 6.

TABLE 6

Glass transition temperature of unsorbed and sorbed-and-locked IOLs

| . | Matrix | Macromer | Sorption by wt % | HDDA polymerization by wt % | Tg of cross-linked polymer matrix | Tg of lockedphoto-responsive shape changing polymer composition |
|---|---|---|---|---|---|---|
| 1 | S14 | HDDA | 20% | Greater than 90% | Less than minus 50 deg C. | Between minus 16 to minus 19 deg C. |
| 2 | S14 | HDDA | 50% | Greater than 90% | Less than minus 50 deg C. | Between minus 16 and minus 19 deg C. |
| 3 | S17 | — | — | — | Minus 11 deg C. | NA |

Example 10 Cytotoxicity Characterization 10 samples of cross-linked polymer matrix S14 were prepared and numbered T1-T10. Samples T1-T8 were sorbed with polymerizable composition Trimethylol propane triacrylate TMPTA, HDDA, Ma1 and Ma2 in duplicate and T9 and T10 were not sorbed. Samples T1, T3, T5, T7 were locked-in using lock-in dose of light while T2, T4, T6, T8 were left unexposed. Samples T1-T10 were evaluated for in-vitro cytotoxicity as per ISO10993-5 "test by direct contact". The cell line as per ISO10993-5 was L929 mouse fibroblast NCTC clone 929 strain L. The negative control was high density polyethylene film and positive control was organotin stabilized polyurethane film. Percent Cell viability was measured by MTT assay. If viability is reduced to <70% of the negative control, it has a cytotoxic potential.

TABLE 7

Cell viability charactrerization.

| No | P2 sorbed | Process condition | % Cell viability of negative control | % Cell viability of positive control | % cell viability of sample |
|---|---|---|---|---|---|
| T1 | TMPTA | Locked-in | 100 | 15 | 90 |
| T2 | TMPTA | Sorbed but unexposed | 100 | 12 | 10 |
| T3 | HDDA | Locked-in | 100 | 13 | 93 |
| T4 | HDDA | Sorbed but unexposed | 100 | 13 | 20 |
| T5 | Ma1 | Locked-in | 100 | 11 | 94 |
| T6 | Ma1 | Sorbed but unexposed | 100 | 7 | 73 |
| T7 | Ma2 | Locked-in | 100 | 9 | 98 |
| T8 | Ma1 | Sorbed but unexposed | 100 | 12 | 84 |
| T9 | Unsorbed | Unsorbed and unexposed | 100 | 8 | 85 |
| T10 | unsorbed | Unsorbed and unexposed | 100 | 10 | 88 |

Results of cell viability experiments demonstrate that the cell viability can be achieved by the choice of the polymerizable composition, by locking-in the photo-responsive shape changing polymer composition

Figure 7:
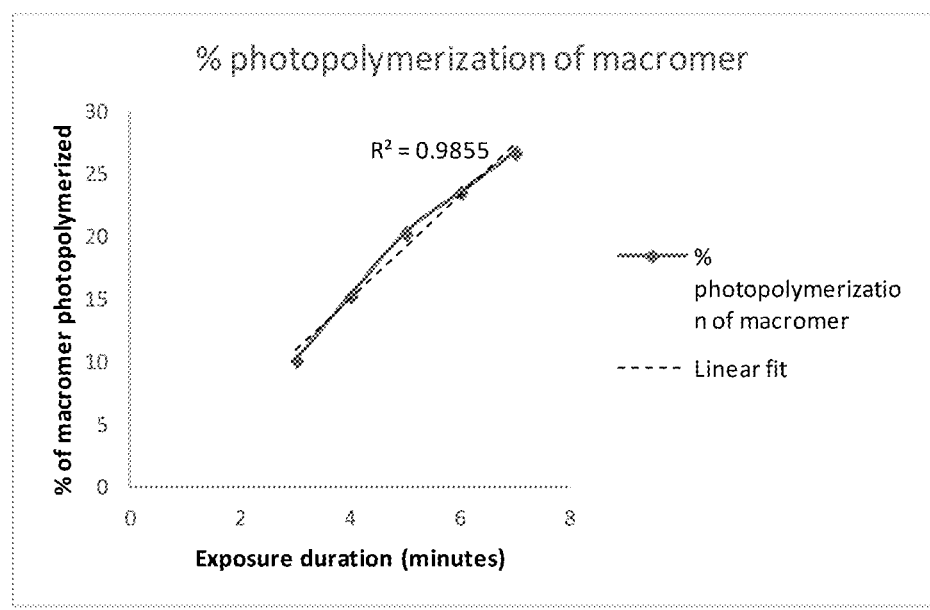
FIG. 7: Design of mold for molding the lens

Example 11 Preparation of Lenses from Photo-Responsive Shape Changing Polymer Composition 10 g of composition S14 was dissolved in 50 ml cyclohexane in a 250 ml round bottom flask. The flask was purged with nitrogen gas for 30 minutes and thereafter sealed with nitrogen blanket. The solution was stirred at 250 rpm and heated at 75° C. for 1.5 h. Cyclohexane was then removed by evaporation using a rotary evaporator leaving behind a viscous prepolymer. The viscous prepolymer was poured in two transparent glass molds 10 as shown in FIG. 7. These two molds were kept on top of each other separated by a spacer. The entire assembly was kept in a holder and exposed to UV light of wavelength 375 nm and uniform intensity distribution of 2 mw/cm$^2$. The intensity was chosen such that there was no photobleaching of the lens, at the same time ensuring complete polymerization. After about 30 minutes the prepolymer polymerized into a colored optical lens without causing photobleaching of the photoinitiator. The wavefront of lenses made by the above method is given in table 9

TABLE 9

Lower and higher order aberrations of the lenses

| No | Optic Diameter (mm) | Defocus term (microns) | Astigmatism (microns) | RMS (microns) | IOL power in air (Diopters) | IOL power in water (Diopters) |
|---|---|---|---|---|---|---|
| 1 | 6 | 0.07 | 0.01 | 0.12 | 78 | 21 |
| 2 | 6 | 0.03 | 0.02 | 0.13 | 78 | 21 |
| 3 | 6 | 0.04 | 0.01 | 0.13 | 78 | 21 |
| 4 | 6 | 0.08 | 0.01 | 0.12 | 78 | 21 |
| 5 | 6 | 0.07 | 0.02 | 0.13 | 78 | 21 |

RMS (root mean square) value of Higher order aberration terms

Figure 8:
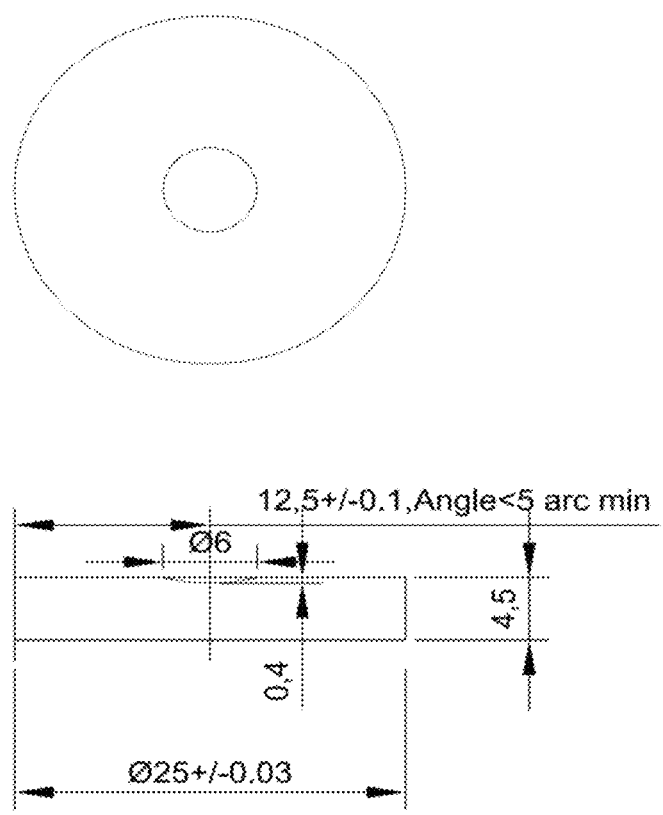
FIG. 8: Comparison of percent transmittance of natural human lens, photo bleached intraocular lens made from photo-responsive shape changing polymer composition and four commercial blue light filtering intraocular lenses

A comparison of percent transmittance of natural human lens, photobleached intraocular lens PB2 as described in table 3 and four commercial blue light filtering intraocular lenses is shown in FIG. 8.

Example 12 Method of Demonstrating Shape Change by Showing Change in Wavefront

If the properties of the surrounding medium and the lens are kept constant then the change in wavefront of a lens on a measurement plane can be calculated by knowing the change in shape of the lens by ray tracing techniques known to person skilled in the art.

Figure 9:
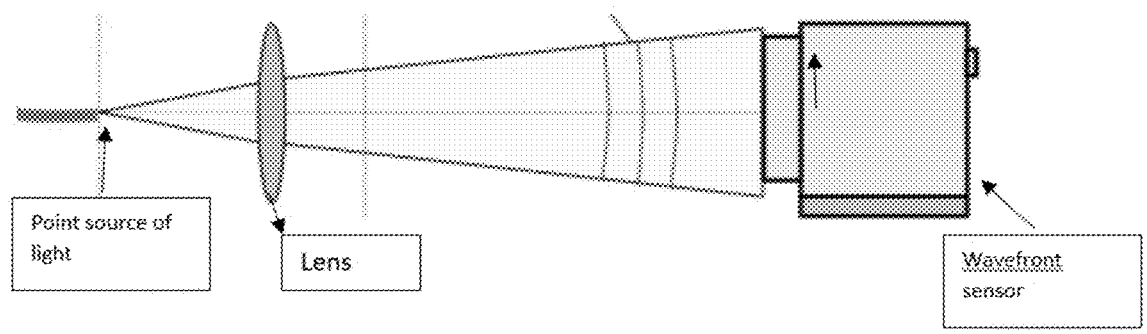
FIG. 9: Experimental Setup to measure wavefront of lenses.
Figure 10:
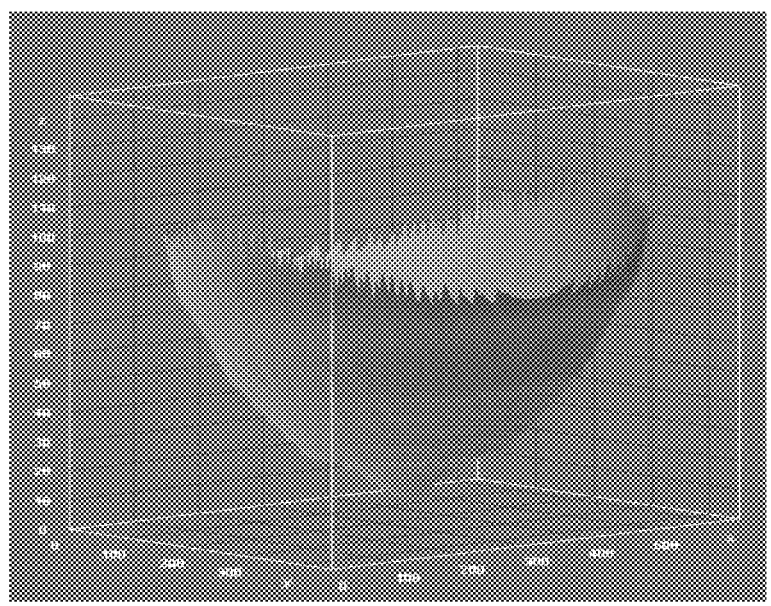
FIG. 10: Spatial Intensity Profile for changing spherical power of the lens.
Figure 11:
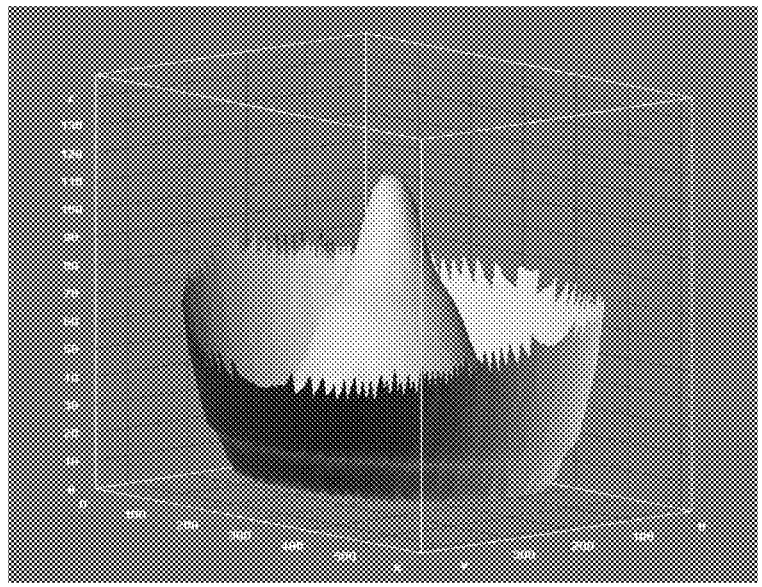
FIG. 11: Spatial intensity profile for changing the higher order spherical aberration.
Figure 12:
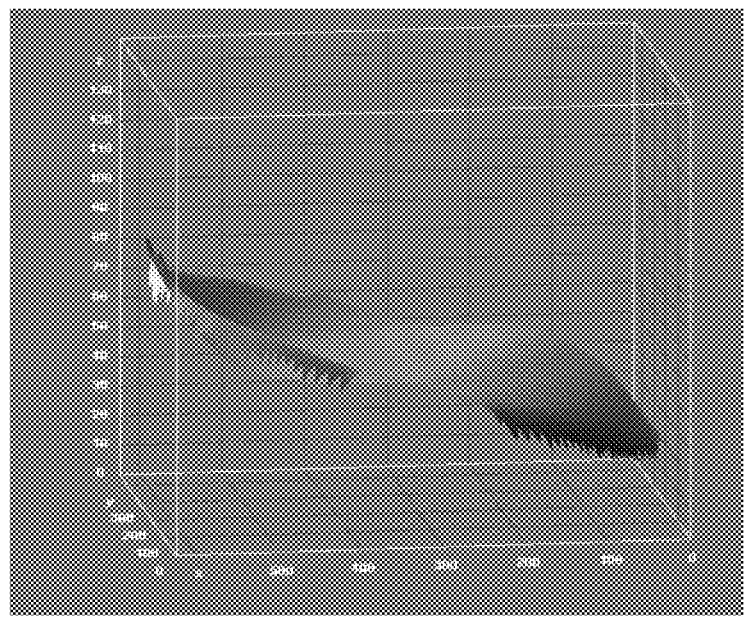
FIG. 12: Spatial intensity profile for changing higher order coma aberration.
Figure 13:
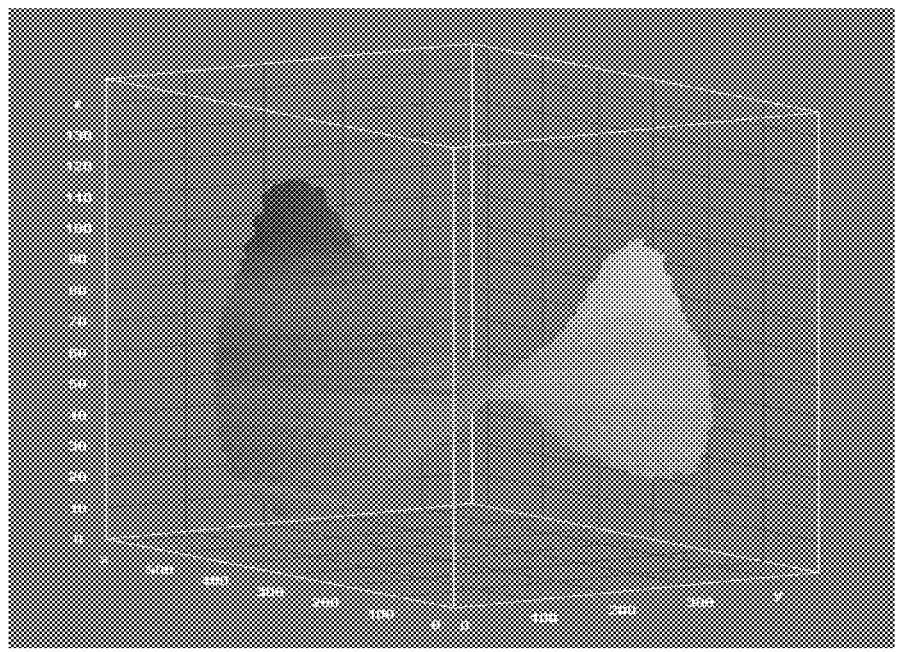
FIG. 13: Spatial intensity profile for changing astigmatism in the lens.

However in optometry and ophthalmology the wavefront of a lens is clinically more relevant than its shape. Wavefront can be mathematically expressed in many ways such as Zernike polynomials, siedel polynomials etc which are inter convertible amongst each. Clinically the eye aberrations are defined by wavefront expressed in lower and higher order Zernike polynomial terms. In ophthalmology and optometry the first 15 Zernike terms are clinically relevant viz the lower order terms called defocus and astigmatism and remaining higher order terms. The table of lower and higher orders terms and their representations are given below FIG. 9 demonstrates the setup to measure the wavefront of a lens. The wavefront sensor (WFS) is a Shack Hartmann wavefront sensor model WFS150-5C from Thorlabs. The WFS is manufacturer calibrated for planar wavefront. An optical test bench was setup as shown in FIG. 9. A point source of light was created using a 20 microns pinhole and a 633 nm laser source focused on the pinhole. The wavefront of the divergent beam was measured at the wavefront sensor at 4.5 mm pupil size. The measured wavefront was found to contain only defocus term. No higher order terms were present.

TABLE 8

Listing of Zernik terms

| Noll Index (j) | Radial Degree (n) | Azimuthal degree (m) | $Z_j$ | Classical Name |
|---|---|---|---|---|
| 1 | 0 | 0 | 1 | Piston (see, Wigner semicircle distribution) |
| 2 | 1 | 1 | $2\rho \sin \phi$ | Tilt (Y-Tilt, vertical tilt) |
| 3 | 1 | −1 | $2\rho \cos \phi$ | Tilt (X-Tilt, horizontal tilt) |
| 4 | 2 | 0 | $\sqrt{8}\rho^2 \sin 2\phi$ | Oblique astigmatism |
| 5 | 2 | −2 | $\sqrt{8}(2\rho^2 - 1)$ | Defocus (longitudinal position) |
| 6 | 2 | 2 | $\sqrt{8}\rho^3 \cos 2\phi$ | Vertical astigmatism |
| 7 | 3 | −1 | $\sqrt{8}(3\rho^3 \sin 3\phi$ | Vertical trefoil |
| 8 | 3 | 1 | $\sqrt{8}(3\rho^3 - 2\rho) \sin \phi$ | Vertical coma |
| 9 | 3 | −3 | $\sqrt{8}(3\rho^3 - 2\rho) \cos \phi$ | Horizontal coma |
| 10 | 3 | 3 | $\sqrt{8}\rho^3 \cos 3\phi$ | Oblique trefoil |
| 11 | 4 | 0 | $\sqrt{10}\rho^4 \sin 4\phi$ | Oblique quadrafoil |
| 12 | 4 | 2 | $\sqrt{10}(4\rho^4 - 3\rho^2) \sin 2\phi$ | Oblique secondary astigmatism |
| 13 | 4 | −2 | $\sqrt{5}(6\rho^4 - 6\rho^2 + 1)$ | Primary spherical |
| 14 | 4 | 4 | $\sqrt{10}(4\rho^4 - 3\rho^3) \cos 2\phi$ | Vertical secondary astigmatism |
| 15 | 4 | −4 | $\sqrt{10}\rho^4 \cos 4\phi$ | Vertical quadrafoil |

A biconvex test IOL of 6 mm diameter and 90% clear aperture was kept in between the pinhole and the wavefront sensor and the distance of the test IOL was varied such that the pinhole is at the focus of the test IOL. When the pinhole is at the focus of the test IOL the defocus term of the measured wavefront will become close to zero. The wavefront was measured at 4.5 mm pupil size and fitted using the first 15 terms of the Zernike polynomials as given in the table below. As expected from an ideal biconvex IOL the only higher order Zernike term present in the measured wavefront was Spherical aberration.

To measure the change in wavefront upon exposure to shape changing dose of light the unexposed IOLs distance from the pinhole is measured when its defocus term was near zero. The IOL was then exposed to shape changing dose of light. After 24 hours the IOL was placed at the same position as before exposure on the test bench and its wavefront was measured again at 4.5 mm pupil. If the shape of the lens has changed, the wavefront of the lens will also change. The table gives below the change in wavefront of the IOL upon exposure to various light intensity patterns.of shape changing dose of light.

Example 13 the changes in the refractive properties of intraocular lens after effecting shape change are summarized below.

TABLE 10 A

Lower order components of Wavefront emerging out of the lens changed upon exposure to different light intensity profiles P1-P4 of shape changing dose of light

| | Intensity pattern | Defocus (microns) pre exposure | Defocus (microns) post exposure | Astigmatism (microns) pre exposure | Astigmatism (microns) post exposure |
|---|---|---|---|---|---|
| 1 | P1 | 0.05 | −0.8 | 0.01 | 0.07 |
| 2 | P2 | 0.01 | 0.2 | 0.02 | 0.02 |
| 3 | P3 | 0.09 | 0.04 | 0.01 | 0.15 |
| 4 | P4 | 0.04 | 0.08 | 0.03 | 0.8 |

TABLE 10B

Higher order components of Wavefront of lenses pre and post exposure with different light intensity profilesP1-P4

| | Intensity Pattern name | Spherical Aberration (microns) | | Coma (microns) | | Trefoil (microns) | | RMS value of HoA (microns) | |
|---|---|---|---|---|---|---|---|---|---|
| | | Pre | Post | Pre | Post | Pre | Post | Pre | Post |
| 1 | P1 | 0.12 | 0.15 | 0.00 | 0.06 | 0.00 | 0.05 | 0.12 | 0.169 |
| 2 | P2 | 0.13 | 0.45 | 0.02 | 0.08 | 0.02 | .03 | 0.133 | 0.458 |
| 3 | P3 | 0.12 | 0.13 | 0.01 | .7 | 0.01 | .16 | 0.120 | 0.729 |
| 4 | P4 | 0.12 | 0.06 | 0.00 | .17 | 0.03 | .15 | 0.123 | 0.234 |

We claim:

1. A photo-responsive colored shape changing polymer composition comprising:
   a) a photoinitiator that absorbs light in the wavelength range of about 400 nm to about 700 nm;
   b) a cross-linked polymer matrix;
   c) a polymerizable composition;
   wherein, exposing the photo-responsive colored shape changing polymer composition to a photobleaching dose of light, in the wavelength range of about 400 nm to about 700 nm, photobleaches the photo-responsive colored shape changing polymer composition such that its maximum absorbance in the visible wavelength region is decreased by at least about 50% from its value prior to exposure to the photobleaching dose of light.

2. The photo-responsive colored shape changing polymer composition as claimed in claim 1, wherein the photoinitiator is selected from the group consisting of thioxanthone fluorenones, anthraquinone, xanthenic dyes and derivatives, acridines and its derivatives, pyrromethenes and derivatives, Polymethines, squarylium and its derivatives, julolidines and derivatives, and combinations thereof.

3. The photo-responsive colored shape changing polymer composition as claimed in claim 2, wherein the photoinitiator comprises 2 ethyl hexyl ester of Eosin-Y.

4. The photo-responsive colored shape changing polymer composition as claimed in claim 1, wherein the cross-linked polymer matrix comprises a mono unsaturated monomer and a cross-linker in cross-linked state.

5. The photo-responsive colored shape changing polymer composition as claimed in claim 1, wherein the cross-linked polymer matrix comprises a mono unsaturated monomer and a macromer in cross-linked state.

6. The photo-responsive colored shape changing polymer composition as claimed in claim 4, wherein the mono unsaturated monomer is selected from the group consisting 2 ethyl hexyl acrylate, butyl acrylate, butyl methacrylate, ethyl acrylate, ethyl methacrylate, 2ethyl hexyl methacrylate, isobutyl acrylate, t butyl acrylate, octyl acrylate, and octyl methacrylate.

7. The photo-responsive colored shape changing polymer composition as claimed in claim 4, wherein the cross-linker is selected from the group consisting of ethylene glycol dimethacrylate, hexane diol diacrylate, ED 20 acrylate, trimethylol propane triacrylate, dipentaerythritol hexaacrylate, and glycerol triacrylate.

8. The photo-responsive colored shape changing polymer composition as claimed in claim 4, wherein the mono unsaturated monomer is selected from the group consisting of 2 ethyl hexyl acrylate, butyl acrylate, butyl methacrylate, ethyl acrylate, ethyl methacrylate, 2ethyl hexyl methacrylate, isobutyl acrylate, t butyl acrylate, octyl acrylate, and octyl methacrylate.

9. The photo-responsive colored shape changing polymer composition as claimed in claim 4, wherein the macromer is obtained by the polymerization of monomer selected from the group consisting of alkylacrylate, alkylmethacrylate, hydroxyalkyl acrylate, hydroxyalkyl methacrylate, acryloyl ester alkyl acrylate, and acryloyl ester alkyl methacrylate, wherein the alkyl functionality comprises a linear or a branched saturated hydrocarbon comprising 2 to 12 carbons.

10. The photo-responsive colored shape changing polymer composition as claimed in claim 1, wherein the cross-linked polymer matrix has a glass transition temperature in the range from about −70° C. to about 10° C.

11. The photo-responsive colored shape changing polymer composition as claimed in claim 1, wherein the polymerizable composition comprises a monomer.

12. The photo-responsive colored shape changing polymer composition as claimed in claim 11, wherein the polymerizable composition comprises a monomer selected from 2 ethyl hexyl acrylate, decyl acrylate, or lauryl acrylate.

13. The photo-responsive colored shape changing polymer composition as claimed in claim 1, wherein the polymerizable composition comprises a cross-linker.

14. The photo-responsive colored shape changing polymer composition as claimed in claim 13, wherein the polymerizable composition contains a cross-linker selected from ethylene glycol dimethacrylate, hexane diol diacrylate, ED 20 acrylate, trimethylol propane triacrylate, dipentaerythritol hexaacrylate, and glycerol triacrylate.

15. The photo-responsive colored shape changing polymer composition as claimed in claim 1, wherein the polymerizable composition comprises a macromer.

16. The photo-responsive colored shape changing polymer composition as claimed in claim 15, comprises a macromer selected from the group consisting of macromer of alkylacrylate, macromer of alkylmethacrylate, macromer of hydroxyalkyl acrylate macromer of hydroxyalkyl methacrylate, macromer of acryloyl ester alkyl acrylate, and macromer of acryloyl ester alkyl methacrylate, in which the alkyl functionality comprises a linear or branched saturated hydrocarbon comprising 2 to 12 carbons.

17. The photo-responsive colored shape changing polymer composition as claimed in claim 1, further comprises a hydrogen donor selected from the group consisting of N phenyl glycine, benzyltrimethylstannanes, thiols, arylsulfinates, sulfur compounds, 1,3-diketone enolates, phosphines, carboxylates, borates, organotins, and amino acids in the presence of phenoxazines, hydroxyl acrylates, hydroxyl methacrylates, and ascorbic acid.

18. The photo-responsive colored shape changing polymer composition as claimed in claim 1, further comprising an electron donour selected from the group consisting of aliphatic or aromatic primary, secondary, tertiary amines, diphenyliodonium chloride, N phenyl glycine (NPGs), benzyltrimethylstannanes, thiols, arylsulfinates, sulfur compounds, 1,3-diketone enolates, phosphines, carboxylates, borates, organotins, and amino acids in the presence of phenoxazines.

19. The photo-responsive colored shape changing polymer composition as claimed in claim 18, wherein the electron donor comprises dimethyl aminoethyl methacrylate.

20. The photo-responsive colored shape changing polymer composition as claimed in claim 1, wherein exposing the composition to a shape changing dose of light, in the wavelength range of about 400 nm to about 700 nm, further changes the shape of the photoresponsive colored shape changing polymer composition by inducing the photoinitiator to cause photopolymerization of the polymerizable composition.

21. The photo-responsive colored shape changing polymer composition as claimed in claim 1, wherein by exposing to a lock-in dose of light, in the wavelength range of about 400 nm to about 700 nm, the refractive properties of the photo-responsive colored shape changing polymer composition are locked in.

22. The photo-responsive colored shape changing polymer composition as claimed in claim 1, wherein the lock-in dose of light lies in the range from about 100 millijoules/cm$^2$ to about 50 Joules/cm$^2$.

23. The photo-responsive colored shape changing polymer composition as claimed in claim 1, wherein the photobleaching dose of light lies in the range about 100 millijoules/cm$^2$ to about 50 Joules/cm$^2$.

24. The photo-responsive colored shape changing polymer composition as claimed in claim 1, fabricated into a colored intraocular lens.wherein the exposure of the coloured intraocular lens to light in the wavelength range from about 400 nm to about 700 nm causes change in spherical power of the colored intraocular lens in the range of about 0.1 to about 50 diopters in air.

25. The photo-responsive colored shape changing polymer composition as claimed in claim 1, fabricated into a colored intraocular lens, wherein the exposure of the colored intraocular lens to light in the wavelength range from about 400 nm to about 700 nm causes change in cylindrical power of the colored intraocular lens in the range of about 0.1 to about 50 diopters in air.

26. The photo-responsive colored shape changing polymer composition as claimed in claim 1, fabricated into a colored intraocular lens, wherein on exposure to the light in the range of about 400 nm to about 700 nm, the changes in the shape of the photo-responsive colored shape changing polymer composition result in changes in rms value of higher order aberrations in the range from about 0.001 microns to about 25 microns in air.

27. A colored intraocular lens comprising:
   a) photoinitiator that absorbs light, in the wavelength range of about 400 nm to about 700 nm,
   b) a cross-linked polymer matrix, and
   c) a polymerizable composition;
   wherein, the colored intraocular lens can be photobleached by exposing the colored intraocular lens to a photobleaching dose of light in the wavelength range of about 400 nm to about 700 nm, such that the maximum absorbance of the colored intraocular lens in the visible wavelength region is decreased by at least 50% from its value prior to exposure to the photobleaching dose of light in the wavelength range of about 400 nm to about 700 nm.

* * * * *

UNITED STATES PATENT AND TRADEMARK OFFICE
CERTIFICATE OF CORRECTION

| | |
|---|---|
| PATENT NO. | : 11,339,281 B2 |
| APPLICATION NO. | : 16/758264 |
| DATED | : May 24, 2022 |
| INVENTOR(S) | : Tanuj Gigras et al. |

Page 1 of 1

It is certified that error appears in the above-identified patent and that said Letters Patent is hereby corrected as shown below:

In the Claims

Claim 8, Line 16, change "compositoin as claimed in claim 4," to --composition as claimed in claim 5,--

Claim 9, Line 37, change "compositoin as claimed in claim 4," to --composition as claimed in claim 5,--

Signed and Sealed this
Third Day of October, 2023

Katherine Kelly Vidal
*Director of the United States Patent and Trademark Office*